United States Patent
Corneillie

(10) Patent No.: US 8,709,823 B2
(45) Date of Patent: Apr. 29, 2014

(54) SINGLE-WAVELENGTH CORRECTION METHOD FOR LUMINESCENT HOMOGENEOUS BIOLOGICAL ASSAY

(75) Inventor: Todd M. Corneillie, Campbell, CA (US)

(73) Assignee: Biophor Diagnostics, Inc., Redwood City, CA (US)

( * ) Notice: Subject to any disclaimer, the term of this patent is extended or adjusted under 35 U.S.C. 154(b) by 128 days.

(21) Appl. No.: 12/838,889

(22) Filed: Jul. 19, 2010

(65) Prior Publication Data

US 2011/0014720 A1 Jan. 20, 2011

Related U.S. Application Data

(60) Provisional application No. 61/271,263, filed on Jul. 17, 2009.

(51) Int. Cl.
*G01N 21/76* (2006.01)
(52) U.S. Cl.
USPC .......................... 436/172; 436/164; 436/166
(58) Field of Classification Search
None
See application file for complete search history.

(56) References Cited

PUBLICATIONS

Tan et al. "Direct detection of Δ9-tetrahydrocannabinol in saliva using a novel homogeneous competitive immunoassay with fluorescence quenching", Analytica Chimica Acta, 2010, v. 658, pp. 187-192.*
Blomberg et al. "Terbium and Rhodamine as Labels in a Homogeneous Time-resolved Fluorometric Energy Transfer Assay of the β Subunit of Human Chorionic Gonadotropin in Serum" Clinical Cllemistry, 1999, v. 45, No. 6, pp. 855-861.*
Upham et al. "Homogeneous Time-Resolved Fluorescence", Integrated Drug Discovery Tecnologies, ed. Mei and Czarnik, CRC Press, 2002, Chapter 11.*
Qin et al. "Time-resolved Fluorescence Resonance Energy Transfer Assay for Point-of-Care Testing of Urinary Albumin" (Title) Clin. Chem., 2003, v. 49, No. 7, pp. 1105-1113.*

* cited by examiner

*Primary Examiner* — Yelena G Gakh
(74) *Attorney, Agent, or Firm* — Mehlin Dean Matthews

(57) ABSTRACT

A method for performing time resolved homogeneous assays using a long-lifetime luminescent dye as a donor. A reaction well containing a sample portion, donor reagent, and acceptor reagent and a matrix well containing a sample portion and donor reagent are excited and the resulting emission from each is measured at a single wavelength associated with the acceptor. The measurement obtained from the matrix well is used to provide a correction for the measurement obtained from the reaction well. The sample may be a biological fluid such as an oral fluid.

20 Claims, 6 Drawing Sheets

SINGLE-WAVELENGTH CORRECTION METHOD FOR LUMINESCENT HOMOGENEOUS BIOLOGICAL ASSAY

CROSS-REFERENCE TO RELATED APPLICATIONS

This application claims priority of U.S. Provisional Application No. 61/271,263, filed Jul. 17, 2009. The aforementioned application is herein expressly incorporated by reference in its entirety.

BACKGROUND OF THE INVENTION

1. Field of the Invention

The present invention relates to biological homogeneous assays. In particular, the invention relates to a corrected method for biological homogeneous assays.

2. Description of Related Art

Ullman et al. first applied luminescence resonance energy transfer (LRET) technology to produce a homogeneous immunoassay using fluorescein and rhodamine as donor and acceptor, respectively. The use of conventional organic fluorophore pairs for homogeneous LRET applications proved not to be practical because the lifetimes of the donor and acceptor were too short, translating to background levels that were too high to make the technology practical. Ideally, a donor luminophore should combine high brightness, high stability and a long luminescence lifetime to be practical for high sensitivity diagnostic applications. The longer luminescent lifetimes of lanthanide donors make them appealing for LRET applications because time-gating techniques can remove the background levels that hamper conventional LRET technologies.

Variations in sample properties including color, viscosity, pH, presence/absence of solids, etc. have the potential to impact assay results. With a heterogeneous assay, this is not usually a concern when the sample result is read by absorbance or luminescence because the sample is washed from the reaction site before the sample is read. With a homogeneous assay, the differences in sample properties can affect the luminescence values. Samples with the same amount of analyte can and do yield different raw luminescent data depending on the properties of the sample. Interfering constituents in samples can absorb the excitation light, donor emission, absorbance emission more or less than a control sample, thereby affecting sample results.

Luminescent lanthanide compounds are known to have long lifetimes (on the order of milliseconds), while conventional organic dyes have lifetimes in the range of nanoseconds. This unique property enables the time gated removal of short-lived background interference that hampers conventional luminescence techniques. As shown in Prior Art FIG. 1, an excitation flash is delivered to a complex biological matrix followed by a short delay (for example 100 µs) to allow unwanted interfering background noise to dissipate. Then data is collected during an integration window that is much longer than the undesirable background (for example 400 µsec) yielding a signal almost free of interference.

Lanthanide dyes can act as donors with conventional organic dye acceptors. When the donor and acceptor are brought into close proximity, excitation energy absorbed by the donor is transferred to the acceptor by a Förster mediated dipole-dipole coupling. The emitted light from the acceptor can be measured in a time-resolved mode, yielding low-noise LRET data compared to data obtained from conventional LRET pairs.

The improved data quality is readily apparent in Prior Art FIG. 2 when comparing the emission of fluorescein (conventional settings) with the emission of an exemplary lanthanide dye, LUMI4-TB (a terbium chelate trademarked by Lumiphore, Inc.) using time-resolved settings. LUMI4-TB is a member of a new class of luminescent hydroxyisophthalamide chelates that combines a high quantum yield (60%) and absorption coefficient and exhibits high stability in aqueous environments. The properties and structure of luminescent hydroxyisophthalamide chelates of lanthanides are discussed in U.S. patent application Ser. No. 12/521,919, "Multi-Color Time Resolved Fluorophores Based on Macrocyclic Lanthanide Complexes," Butlin, Corneillie, and Xu; filed Jan. 25, 2008.

Prior Art FIG. 2 demonstrates the reduced background and improved linear range achieved with time-resolved luminescence. In this experiment, fluorescein exhibits a linear range down to ~1.0 nM (conventional settings). Time-resolved measurements of LUMI4-TB exhibit a much larger linear range (down to below 10 pM), which is achieved by gating out short-lived interference attributable to the lamp source, optics, matrix components, etc.

Prior Art FIG. 3 shows the absorption and emission spectra for an exemplary lanthanide dye, LUMI4-TB. Broad absorption of the sensitizing 2-hydroxyisophthalamide chelating unit is centered at 340 nm. The emission spectrum is characteristic of luminescent terbium complexes with the dominant peaks centered at 545 nm and 490 nm. The large separation between absorption and emission peaks (Stokes Shift) eliminates the reabsorption of emitted luminescence that hampers the performance of conventional organic dyes.

A schematic representation of an exemplary competitive, homogeneous assay technology is shown in Prior Art FIGS. 4A, 4B, 4C, and 4D. As shown in FIG. 4A, an antibody 405 is coupled to an acceptor luminophore 410 (e.g., fluorescein) to serve as an acceptor reagent with binding sites 415 that are specific for analyte 420 and the competitor conjugate donor 425 that is derived from the analyte component and a luminophore (e.g., LUMI4-TB). As shown in FIG. 4A, the concentration of the analyte 420 is low relative to the concentration of the competitor conjugate donor 425.

As shown in FIG. 4B, excitation energy is first absorbed by the competitor conjugate donor 425. When the donor and acceptor are brought into close proximity (e.g., through binding to the antibody 405), energy is transferred from the competitor conjugate donor 425 to the acceptor 410 by a Förster mediated dipole-dipole coupling. The acceptor 410 subsequently produces a LRET signal at the wavelength of the acceptor luminophore 410. In the presence of a low amount of analyte the LRET signal is near its maximum, as the competitor conjugate donor 425 binds unimpeded to the analyte-specific antibody 405.

As shown in FIG. 4C and FIG. 4D, the concentration of the analyte 420 is high relative to the concentration of the competitor conjugate donor 425, and the LRET signal is low, since the analyte 420 out competes the competitor conjugate donor 425 that carries the lanthanide donor.

For laboratory tests, homogeneous assay methods are preferable to heterogeneous methods because test procedures are simple and fast, requiring no washing steps. LRET is a homogeneous method that does not require enzyme inactivation or reformation to generate a signal and avoids some of the limitations of other homogeneous assay technologies. This assay platform relies on LRET between complementary molecules labeled with either a lanthanide donor or an acceptor (e.g., fluorescein). The key component to a practical LRET assay is the donor luminophore, which ideally should combine high brightness, high stability and low background to attain the sensitivity required for detecting drugs of abuse in oral fluid. The longer lifetimes of lanthanide donors make them appealing for LRET applications because time-gating techniques remove the background levels that hamper conventional LRET technologies. LUMI4-TB incorporates four isophthalamide chelating units and achieves an unparalleled level of brightness when coordinated to terbium. The luminescent lanthanide technology has been combined with high affinity and high specificity antibodies for drugs to develop this oral fluid drug assay technology.

Oral fluid has become an important matrix for testing because samples are relatively easy to collect, are more reflective of recent use and more closely tracking blood levels, the reference standard. Testing for drugs in oral fluid presents a challenge for current homogeneous laboratory testing technologies and point-of-care testing (POCT) products, which were developed for testing in urine. While detection levels for laboratory and lateral flow POCT assays for urine are in the 50-2000 ng/mL range for drugs, the levels in oral fluid are sometimes an order of magnitude or more lower. More sensitive technologies are needed.

In order to correct for the variability between samples that can occur in a homogeneous assay, techniques involving additional measurements may be used. For example, U.S. Pat. No. 6,861,264, "Method of Measuring the Luminescence Emitted in a Luminescent Assay," Mabile et al, issued Mar. 1, 2005, teaches the use of measurements taken at two difference wavelengths emitted by a single sample volume.

Thus there is a need for a rapid, homogeneous assay method for measuring parent drug compounds in oral fluid. There is also a need for a method of measurement correction that is applicable at a single wavelength.

BRIEF SUMMARY OF THE INVENTION

The present invention provides a method for performing time resolved homogeneous assays using a long-lifetime luminescent dye as a donor. A reaction well containing a sample portion, donor reagent, and acceptor reagent and a matrix well containing a sample portion and reference luminophore (e.g., donor reagent) are excited and the resulting emission from each is measured at a single wavelength associated with the acceptor. The measurement obtained from the matrix well is used to provide a correction for the measurement obtained from the reaction well. The sample may be a biological fluid such as an oral fluid.

In one embodiment of the invention, the donor reagent includes a lanthanide dye. The dye may be a hydroxisophthalamide-based luminescent or a macrocyclic hydroxisophthalamide-based luminescent (e.g., LUMI4-TB).

In another embodiment, the correction is obtained by a calculation involving the measured intensities of the reaction well and relevant matrix well. In a further embodiment the corrected intensity is obtained by taking the ratio of the reaction well intensity to the matrix well intensity.

BRIEF DESCRIPTION OF THE DRAWINGS

Prior Art

Prior Art

Prior Art

Prior Art

Prior Art

Prior Art

Prior Art

DETAILED DESCRIPTION OF THE INVENTION

Figure 1:
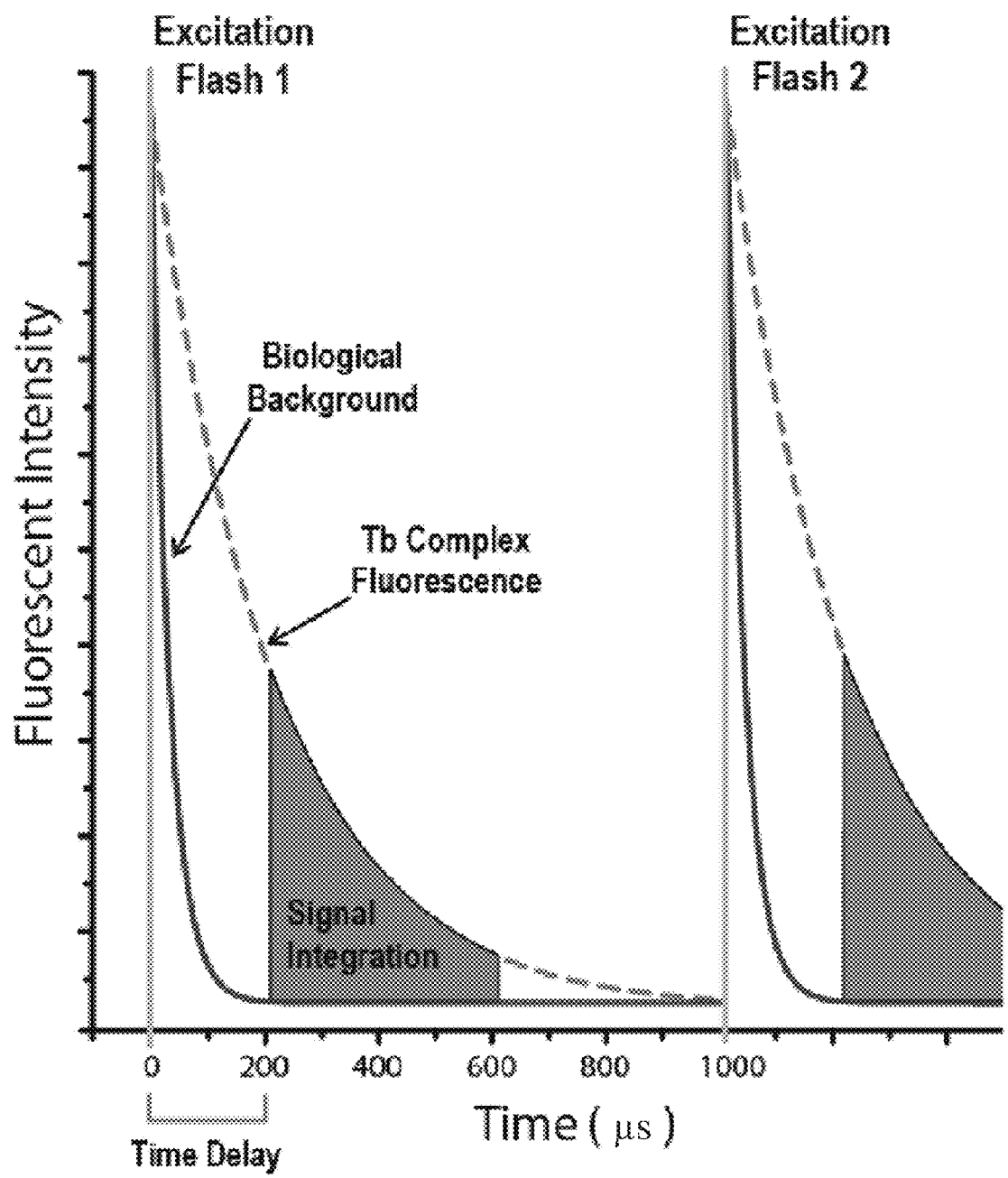
FIG. 1 shows the temporal evolution of a luminescent process involving a long-lifetime dye.
Figure 2:
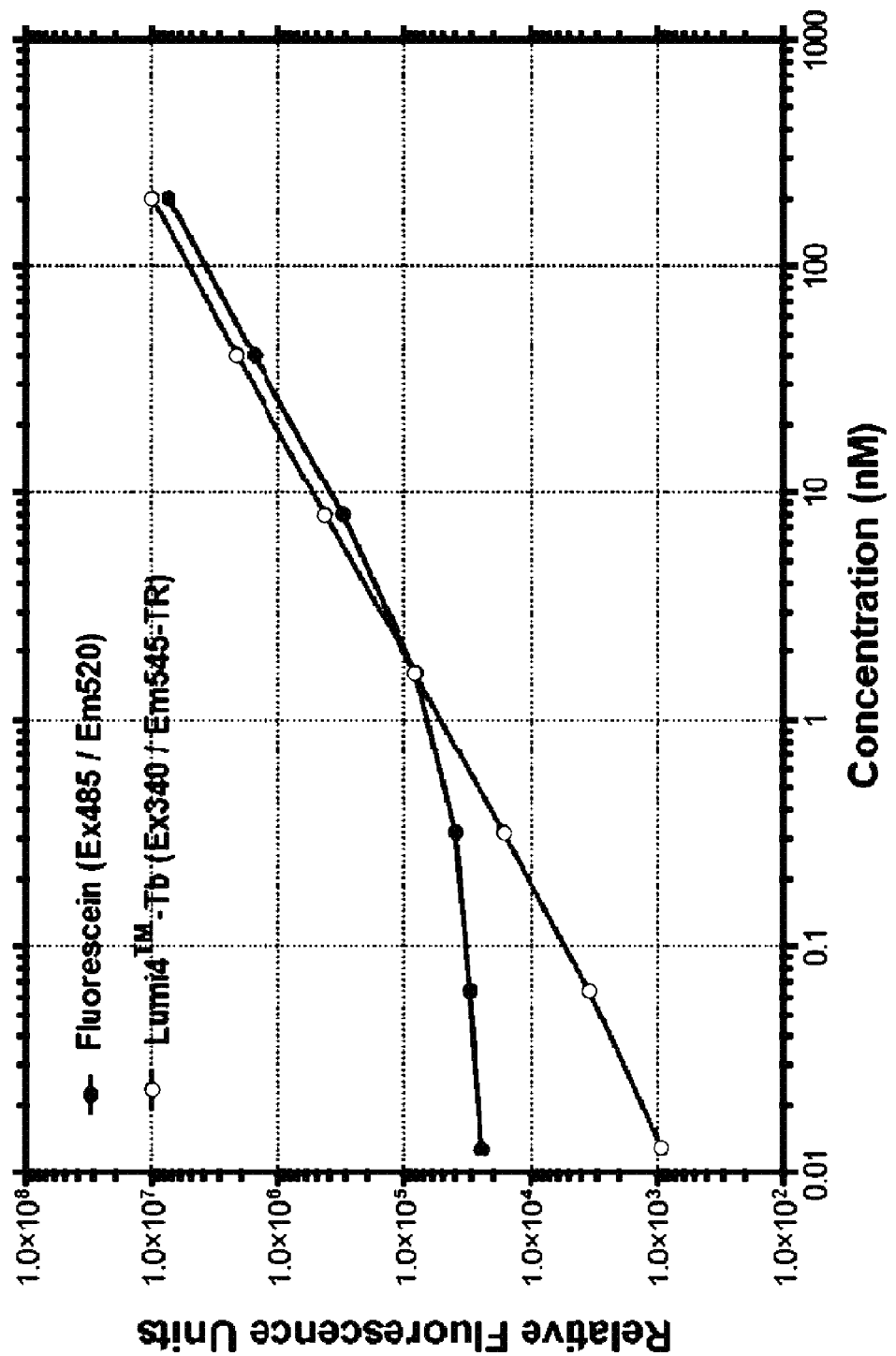
FIG. 2 shows a plot of luminescent intensity versus concentration for fluorescein and LUMI4-TB.

A single assay in accordance with the present invention involves the optical excitation of at least two discrete volumes (e.g., reaction well and matrix well) and the measurement of the luminescent response at a single wavelength. The preparation of a reaction well solution involves mixing an antibody-luminophore reagent and sample, followed by the addition of a competitor-luminophore conjugate. The preparation of a matrix well involves the mixing of a sample and a reference luminophore (e.g., competitor-luminophore conjugate).

In the examples that follow, multiple assays are performed for seven drugs using a single microtiter plate. The details provided in the examples should not be construed as limiting the subject of invention. Each drug assay requires a unique antibody-luminophore reagent that is specific for the drug being evaluated. To simplify the testing procedure and improve sample throughput, the various competitor conjugates are formulated into a single competitor solution. The assay technology yields a rapid result with only two reagents (antibody-luminophore and competitor luminophore conjugate) and is amenable to automation in a laboratory setting.

In a homogeneous LRET experiment, there are two dyes: donor and acceptor. When donor and acceptor are brought into close proximity, LRET occurs. The close proximity may be obtained through antibody-antigen binding events, receptor-ligand interactions, etc. The reaction should be composed of a donor luminophore, acceptor luminophore and sample. The matrix should be composed of the sample and a luminophore that absorbs and emits at the same or similar wavelengths as those being used in the reaction well.

A simple ratio of the value for the reaction well divided by the value for the matrix well value yields a value corrected for sample differences, although more complicated mathematics can be used. For example, correct raw data for sample interference using the equation $Cx=Sx/Mx$ where $Cx$ is the corrected result, $Sx$ is the reaction signal and $Mx$ is the matrix signal for the same sample.

Exemplary Instrument System

A time resolved luminescence reader capable of accurate reading of 96 well microplates (PerkinElmer ENVISION microplate reader) was used for measurements in the following examples. The instrument provided an excitation capability at 340 nm with a 30-60 nm band pass, and 520 nm centered emission detection with 5-30 nm bandpass filters. The instrument should have timing control, the capability for delay (e.g., 100 usec), integration window (e.g., 100 usec) and cycle settings (e.g., 10-100 cycles). A computer interfaced to the reader captures and reports results.

Example 1

Seven different assays for the following drugs: (Amphetamine (AMP), Cocaine (COC), Methamphetamine (MET), Morphine (MOR), Phencyclidine (PCP), Tetrahydrocannabinol (THC), 3,4-methylenedioxy-N-methylamphetamine (MDMA, XTC); were performed with a coffee colored oral fluid sample that was successively diluted with a colorless, clear buffer yielding sample dilutions of 2×, 4×, 8×, 16×, 32× and 64×. All of these samples were negative for the drug analyzed.

Materials

Donor Reagent: LUMI4-TB conjugated to analyte competitor (analyte-Tb conjugates combined into single multianalyte competitor solution)

Acceptor Reagent: Fluorescein acceptor conjugated to analyte-specific antibodies oral fluid sample
dilution buffer Assay Procedure 1. Dispense 25 μL of each sample into all 9 wells of a single row in the microtiter plate.
2. Dispense 25 μL of each control into all 9 wells of rows 7 (Negative control) and 8 (positive control).
3. Add 75 μL of Acceptor Reagents Amphetamine (AMP) acceptor reagent, Cocaine (COC) acceptor reagent, Methamphetamine (MET) acceptor reagent, Morphine (MOR) acceptor reagent, Phencyclidine (PCP) acceptor reagent, Tetrahydrocannabinol (THC) acceptor reagent, 3,4-methylenedioxy-N-methylamphetamine (MDMA) acceptor reagent and the Blank Matrix Solution to columns 1-8, respectively.
4. Gently mix plate on shaker at room temperature for 5 minutes.
5. Add 75 μL of Multi-Donor Reagent to all wells in each column.
6. Mix plate gently for at least 30 seconds and read plate at least 3 minutes after addition of Multi-Donor Reagent.

The reaction well for each drug included: sample (25 uL), acceptor reagent (75 uL), donor reagent (75 uL). The first matrix well included: sample (25 uL), donor reagent (75 uL), solution added (75 uL) to yield same volume as reaction wells. The second matrix well (less volume) included: sample (25 uL) and donor reagent (75 uL). No "makeup" solution was added to the second matrix well.

The time-resolved luminescence plate reader instrument was set for a 100 μs delay, a 100 μs integration window and 100 cycles. A computer interfaced to the reader captured and reported the results shown in Table 1 below.

Data Treatment

The correction was made using luminescence measurements at a single wavelength (single emission bandpass filter is used). Reaction and matrix wells are read at a wavelength where acceptor emission can be detected (520 nm in this example). Note that donor and acceptor emission are visible in the acceptor wavelength window in this example. Any changes in the luminescence value for the sample is also reflected in the value for the matrix. Dividing these values effectively corrects the luminescence reading for sample differences. A control or calibrator sample is measured the same way (reaction well and matrix well).

TABLE 1

| Sample | Dilution of oral fluid | Raw data AMP 0 ng/mL | COC 0 ng/mL | MET 0 ng/mL | MOR 0 ng/mL | PCP 0 ng/mL | THC 0 ng/mL | XTC 0 ng/mL | MATRIX same volume | MATRIX less volume |
|---|---|---|---|---|---|---|---|---|---|---|
| 1 | 2x | 11815 | 9192 | 15967 | 21295 | 12709 | 5275 | 12984 | 3046 | 3321 |
| 2 | 4x | 15904 | 12393 | 21359 | 27098 | 16825 | 6802 | 17703 | 3630 | 4038 |
| 3 | 8x | 17957 | 14666 | 24639 | 31305 | 19392 | 8155 | 20624 | 4301 | 4535 |
| 4 | 16x | 20154 | 16008 | 27135 | 34108 | 21489 | 8993 | 23330 | 4835 | 5171 |
| 5 | 32x | 21220 | 16465 | 28161 | 35250 | 21829 | 9355 | 23702 | 4935 | 5285 |
| 6 | 64x | 21880 | 16949 | 28771 | 36310 | 22510 | 9980 | 24484 | 5143 | 5478 |
| Negative control | | 22202 | 17153 | 29528 | 35911 | 23158 | 10537 | 25246 | 5162 | 6288 |
| Positive Control | | 11587 | 12696 | 15224 | 22217 | 14012 | | 15535 | 5237 | 6080 |

| | | Corrected data - Reaction well value/Matrix (same volume) value | | | | | | |
|---|---|---|---|---|---|---|---|---|
| Sample | Dilution of oral fluid | AMP 0 ng/mL | COC 0 ng/mL | MET 0 ng/mL | MOR 0 ng/mL | PCP 0 ng/mL | THC 0 ng/mL | XTC 0 ng/mL |
| 1 | 2x | 3.88 | 3.02 | 5.24 | 6.99 | 4.17 | 1.73 | 4.26 |
| 2 | 4x | 4.38 | 3.41 | 5.88 | 7.47 | 4.63 | 1.87 | 4.88 |
| 3 | 8x | 4.18 | 3.41 | 5.73 | 7.28 | 4.51 | 1.9 | 4.8 |
| 4 | 16x | 4.17 | 3.31 | 5.61 | 7.05 | 4.44 | 1.86 | 4.83 |
| 5 | 32x | 4.3 | 3.34 | 5.71 | 7.14 | 4.42 | 1.9 | 4.8 |
| 6 | 64x | 4.25 | 3.3 | 5.59 | 7.06 | 4.38 | 1.94 | 4.76 |
| Negative control | | 4.3 | 3.32 | 5.72 | 6.96 | 4.49 | 2.04 | 4.89 |
| Positive Control | | 2.21 | 2.42 | 2.91 | 4.24 | 2.68 | | 2.97 |
| | AVERAGE (1-6) | 4.19 | 3.3 | 5.63 | 7.17 | 4.43 | 1.87 | 4.72 |
| | SD | 0.17 | 0.15 | 0.22 | 0.18 | 0.15 | 0.07 | 0.23 |
| | CV | 0.04 | 0.04 | 0.04 | 0.02 | 0.03 | 0.04 | 0.05 |
| Negative Control | REL ERR | −0.03 | −0.01 | −0.02 | 0.03 | −0.01 | −0.09 | −0.03 |

| | | Corrected data - Reaction well value/Matrix (less volume) value | | | | | | |
|---|---|---|---|---|---|---|---|---|
| Sample | Dilution of oral fluid | AMP 0 ng/mL | COC 0 ng/mL | MET 0 ng/mL | MOR 0 ng/mL | PCP 0 ng/mL | THC 0 ng/mL | XTC 0 ng/mL |
| 1 | 2x | 3.56 | 2.77 | 4.81 | 6.41 | 3.83 | 1.59 | 3.91 |
| 2 | 4x | 3.94 | 3.07 | 5.29 | 6.71 | 4.17 | 1.68 | 4.38 |
| 3 | 8x | 3.96 | 3.23 | 5.43 | 6.9 | 4.28 | 1.8 | 4.55 |

TABLE 1-continued

| | | | | | | | |
|---|---|---|---|---|---|---|---|
| 4 | 16x | 3.9 | 3.1 | 5.25 | 6.6 | 4.16 | 1.74 | 4.51 |
| 5 | 32x | 4.02 | 3.12 | 5.33 | 6.67 | 4.13 | 1.77 | 4.48 |
| 6 | 64x | 3.99 | 3.09 | 5.25 | 6.63 | 4.11 | 1.82 | 4.47 |
| Negative control | | 3.53 | 2.73 | 4.7 | 5.71 | 3.68 | 1.68 | 4.01 |
| Positive Control | | 1.91 | 2.09 | 2.5 | 3.65 | 2.3 | | 2.56 |
| AVERAGE (1-6) | | 3.89 | 3.06 | 5.23 | 6.65 | 4.11 | 1.73 | 4.38 |
| SD | | 0.17 | 0.16 | 0.22 | 0.16 | 0.15 | 0.09 | 0.24 |
| CV | | 0.04 | 0.05 | 0.04 | 0.02 | 0.04 | 0.05 | 0.05 |
| Negative Control REL ERR | | 0.1 | 0.12 | 0.11 | 0.16 | 0.12 | 0.03 | 0.09 |

Discussion of Results

In this assay, the luminescence is inversely proportional to the concentration of analyte. In general, higher values indicate less analyte is present with a negative sample having the highest value. This sample was known to be free of all of the drug analytes tested. Yet, it is clear that the raw luminescent values in all of the assays including the matrix wells increase as the sample is diluted and the color of the sample becomes lighter. The color of the sample is affecting the result. The raw data falsely indicate that Sample 1 is more positive than the positive control for cocaine (COC), morphine (MOR), phencyclidine (PCP) and 3,4-methylenedioxy-N-methylamphetamine (XTC). Sample 2 even appears to be positive for cocaine (COC) when looking at the raw data. However, the corrected data (using either the same volume or less volume matrix) yields the expected negative results for all samples, and the average value for all samples for a given analyte are very close to the Negative Control as expected.

Example 2

Two different assays for the following drugs: COC, MOR; were performed with a coffee colored oral fluid sample that was successively diluted with a colorless, clear buffer yielding sample dilutions of 2x, 4x, 8x, 16x, 32x and 64x. The samples were initially negative for the drug analyzed. Once the samples were diluted with buffer, the samples were then split into aliquots. Some aliquots were spiked at one of the following drug concentrations: COC: 10 ng/mL, 20 ng/mL, MOR: 40 ng/mL Materials
  Donor Reagent: LUMI4-TB conjugated to analyte competitor (analyte-Tb conjugates combined into single multi-analyte competitor solution)
  Acceptor Reagent: Fluorescein acceptor conjugated to analyte-specific antibodies
  oral fluid sample
  dilution buffer
  analyte solutions for spiking Assay Procedure
  1. Dispense 25 μL of each sample into all 7 wells of a single row in the microtiter plate.
  2. Dispense 25 μL of each control into all 7 wells of rows 7 (Negative control) and 8 (positive control).
  3. Add 75 μL of Acceptor Reagents Cocaine (COC) acceptor reagent (columns 1-3), Morphine (MOR) acceptor reagent (columns 4-5) and the Blank Matrix Solution (column 6) to the indicated columns.
  4. Gently mix plate on shaker at room temperature for 5 minutes.
  5. Add 75 μL of Multi-Donor Reagent to all wells in each column.
  6. Mix plate gently for at least 30 seconds and read plate at least 3 minutes after addition of Multi-Donor Reagent.

The Time-resolved luminescence plate reader instrument was set for a 100 μs delay, a 100 μs integration window and 100 cycles. A computer interfaced to the reader captured and reported results shown in Table 2.

The reaction well for each drug included: sample (25 uL), acceptor reagent (75 uL), donor reagent (75 uL). The first matrix well included: sample (25 uL), donor reagent (75 uL), solution added (75 uL) to yield same volume as reaction well. The second matrix well (less volume) included: sample (25 uL) and donor reagent (75 uL). No "makeup" solution was added to the second matrix well.

Data Treatment

The correction was made using luminescence measurements at a single wavelength (single emission bandpass filter is used). Reaction and matrix wells are read at a wavelength where acceptor emission can be detected (520 nm in this example). Note that donor and acceptor emission are visible in the acceptor wavelength window in this example. Any changes in the luminescence value for the sample is also reflected in the value for the matrix. Dividing these values effectively corrects the luminescence reading for sample differences. A control or calibrator sample is measured the same way (reaction well and matrix well).

TABLE 2

| Sample | Dilution of oral fluid | Raw data COC 0 ng/mL | COC 20 ng/mL | COC 10 ng/mL | MOR 0 ng/mL | MOR 40 ng/mL | Matrix same vol | Matrix less volume |
|---|---|---|---|---|---|---|---|---|
| 1 | 2x | 9658 | 7099 | 8086 | 21904 | 11076 | 3039 | 2831 |
| 2 | 4x | 12140 | 9002 | 9597 | 27188 | 12982 | 3756 | 3383 |
| 3 | 8x | 14776 | 10182 | 11302 | 31252 | 15695 | 4199 | 3785 |
| 4 | 16x | 15391 | 10913 | 12647 | 33129 | 16291 | 4641 | 4102 |
| 5 | 32x | 16846 | 11539 | 13153 | 34851 | 17122 | 4763 | 4569 |
| 6 | 64x | 18084 | 12382 | 13862 | 35906 | 17935 | 5227 | 4843 |
| Negative control | | 17999 | 17242 | 17162 | 35296 | 34420 | 5294 | 4770 |
| Positive Control | | 12508 | 12121 | 12013 | 19345 | 19081 | 5243 | 4965 |

TABLE 2-continued

Corrected data - Reaction well value/Matrix (same volume) value

| Sample | Dilution of oral fluid | COC 0 ng/mL | COC 20 ng/mL | COC 10 ng/mL | MOR 0 ng/mL | MOR 40 ng/mL |
|---|---|---|---|---|---|---|
| 1 | 2x | 3.18 | 2.34 | 2.66 | 7.21 | 3.64 |
| 2 | 4x | 3.23 | 2.4 | 2.56 | 7.24 | 3.46 |
| 3 | 8x | 3.52 | 2.42 | 2.69 | 7.44 | 3.74 |
| 4 | 16x | 3.32 | 2.35 | 2.73 | 7.14 | 3.51 |
| 5 | 32x | 3.54 | 2.42 | 2.76 | 7.32 | 3.59 |
| 6 | 64x | 3.46 | 2.37 | 2.65 | 6.87 | 3.43 |
| | Negative control | 3.4 | 3.26 | 3.24 | 6.67 | 6.5 |
| | Positive Control | 2.39 | 2.31 | 2.29 | 3.69 | 3.64 |
| | AVERAGE (1-6) | 3.37 | 2.38 | 2.67 | 7.2 | 3.56 |
| | SD | 0.15 | 0.04 | 0.07 | 0.19 | 0.12 |
| | CV | 0.05 | 0.02 | 0.03 | 0.03 | 0.03 |
| Negative Control | REL ERR | −0.01 | | | 0.08 | |

Corrected data - Reaction well value/Matrix (less volume) value

| Sample | Dilution of oral fluid | COC 0 ng/mL | COC 20 ng/mL | COC 10 ng/mL | MOR 0 ng/mL | MOR 40 ng/mL |
|---|---|---|---|---|---|---|
| 1 | 2x | 3.41 | 2.51 | 2.86 | 7.74 | 3.91 |
| 2 | 4x | 3.59 | 2.66 | 2.84 | 8.04 | 3.84 |
| 3 | 8x | 3.9 | 2.69 | 2.99 | 8.26 | 4.15 |
| 4 | 16x | 3.75 | 2.66 | 3.08 | 8.08 | 3.97 |
| 5 | 32x | 3.69 | 2.53 | 2.88 | 7.63 | 3.75 |
| 6 | 64x | 3.73 | 2.56 | 2.86 | 7.41 | 3.7 |
| | Negative control | 3.77 | 3.61 | 3.6 | 7.4 | 7.22 |
| | Positive Control | 2.52 | 2.44 | 2.42 | 3.9 | 3.84 |
| | AVERAGE (1-6) | 3.68 | 2.6 | 2.92 | 7.86 | 3.89 |
| | SD | 0.17 | 0.08 | 0.1 | 0.32 | 0.16 |
| | CV | 0.05 | 0.03 | 0.03 | 0.04 | 0.04 |
| Negative Control | REL ERR | −0.02 | | | 0.06 | |

Discussion of Results

In this assay, the luminescence is inversely proportional to the concentration of analyte. In general, higher values indicate less analyte is present with a negative sample having the highest value. Samples were spiked with analytes at the concentrations indicated in the top row of the results tables above. It is clear that the raw luminescent values for a given spike level group in all of the assays including the matrix wells increase as the sample is diluted and the color of the sample becomes lighter. The color of the sample is affecting the result. For the cocaine (COC) 0 ng/mL group, the raw data falsely indicate that Samples 1 & 2 were more positive than the positive control for cocaine (COC). Note that the corrected values using either matrix yield the expected result (all samples are negative in this group). The corrected data (using either matrix to correct) are consistent for a given group as the oral fluid color is diluted.

Cocaine was spiked at 20 ng/mL in the positive control for the cocaine tests. As can be seen in the 20 ng/mL COC test column, the raw data yield differing results for samples spiked at the same level, and the values correlate with the intensity of the color of the sample. The correction factor removes the color bias, and all of the samples test near the level of the positive control. The raw data for samples spiked with 10 ng/mL cocaine show the same trend. The corrected values indicate that there is less than 20 ng/mL in the samples, while the raw data for these same samples indicate that the 2x, 4x and 8x samples have greater than 20 ng/mL cocaine and the 16x, 32x and 64x samples have less than 20 ng/mL drug.

For the morphine (MOR) 0 ng/mL group, raw luminescent values increase as the sample is diluted and the color of the sample becomes lighter. Note that the corrected values using either matrix yield the expected result (all samples are negative in this group).

Morphine was spiked at 40 ng/mL in the positive control for the morphine tests. As can be seen in the 40 ng/mL morphine (MOR) test column, the raw data yield differing results for samples spiked at the same level, and the values correlate with the intensity of the color of the sample. The correction factor removes the color bias, and all of the samples test near the level of the positive control.

Example 3

Seven different assays for the following drugs: Amphetamine (AMP), Cocaine (COC), Methamphetamine (MET), Morphine (MOR), Phencyclidine (PCP), Tetrahydrocannabinol (THC), 3,4-methylenedioxy-N-methylamphetamine (XTC); were performed with oral fluid samples, which contained drug analytes or interfering species. The samples results were compared against cutoff calibrators. The cutoff levels were used for determining whether a sample was Positive (POS) or Negative (−) for a specific analyte. The cutoff levels used were as follows: amphetamine (AMP)—50 ng/mL, cocaine (COC)—20 ng/mL, methamphetamine (MET)—50 ng/mL, morphine (MOR)—40 ng/mL, phencyclidine (PCP)—10 ng/mL, tetrahydrocannabinol (THC)—4 ng/mL, 3,4-methylenedioxy-N-methylamphetamine (XTC)—50 ng/mL. The assay results were compared with the results of quantitative analysis by GC/MS.

Materials

Specific Acceptor Reagents: Amphetamine (AMP), Cocaine (COC), Methamphetamine (MET), Morphine (MOR), Phencyclidine (PCP), Tetrahydrocannabinol (Δ9-THC), THC) and 3,4-methylenedioxy-N-methylamphetamine (MDMA). Antibodies conjugated to an acceptor fluorophore in buffer with preservative.

Multi-Donor Reagent: Donor luminophore conjugated to amphetamine, cocaine, methamphetamine, morphine, phencyclidine, tetrahydrocannabinol (Δ9-THC) and 3,4-methylenedioxy-N-methylamphetamine (MDMA) drug derivatives in buffer with preservative.

Matrix Blank Reagent
Neat oral fluid samples

Assay Procedure

1. Allow reagents and assay components to warm room temperature (20-25° C., 68-77° F.).
2. Mix oral fluid samples thoroughly before use.
3. Dispense 25 μL of each sample into all 8 wells of a single column in the microtiter plate. Up to 10 samples may be assayed in each plate in columns 1-10.
4. Dispense 25 μL of each calibrator into all 8 wells of columns 11 (Negative) and 12 (Cutoff).
5. Add 75 μL of Acceptor Reagents Amphetamine (AMP) acceptor reagent, Cocaine (COC) acceptor reagent, Methamphetamine (MET) acceptor reagent, morphine (MOR) acceptor reagent, Phencyclidine (PCP) acceptor reagent, Tetrahydrocannabinol (THC) acceptor reagent, 3,4-methylenedioxy-N-methylamphetamine (MDMA) acceptor reagent and the Blank Matrix Solution to rows 1-8, respectively.
6. Gently mix plate on shaker at room temperature for at least 5 minutes.
7. Add 75 μL of Multi-Donor Reagent to all wells in each row.
8. Mix plate gently for at least 30 seconds and start reading plate 3-5 minutes following addition of the Multi-Donor Reagent.

The Time-resolved luminescence plate reader instrument was set for a 100 μs delay, a 100 μs integration window and 100 cycles. A computer interfaced to the reader captured and reported results shown in Table 3.

Calibration and Quality Control

A cutoff calibrator is required to determine whether the concentration of the target analyte is above or below the cutoff level in an oral fluid sample. Positive and negative controls should be within +50% and −50% of the individual analyte cutoffs and users should follow the appropriate federal, state and local guidelines concerning the running of external quality controls.

Data Treatment

Correct raw data for sample interference using the equation $Cx=Sx/Mx$ where $Cx$ is the corrected result, $Sx$ is the sample, calibrator or control signal and $Mx$ is the matrix signal for the same sample, calibrator or control. Compare matrix-corrected sample, control and negative calibrator values to those of the matrix-corrected cutoff calibrator signal. Corrected samples and controls with a value less than the corrected cutoff calibrator are considered presumptive positive. Corrected samples and controls with values equal to or greater than the corrected cutoff calibrator are considered negative.

TABLE 3

| | \multicolumn{10}{c}{520 nm Raw Data} | | | | | | | | | |
|---|---|---|---|---|---|---|---|---|---|---|
| AMP | 17574 | 13582 | 15593 | 32021 | 16523 | 17348 | 18967 | 35263 | 43899 | 22352 |
| COC | 38040 | 37218 | 38615 | 30636 | 38005 | 36209 | 29775 | 36430 | 41798 | 32676 |
| MET | 15166 | 15399 | 16186 | 33965 | 16266 | 14638 | 20835 | 37051 | 54050 | 24676 |
| MOR | 36432 | 36367 | 37451 | 30562 | 37695 | 34815 | 17573 | 28693 | 40909 | 20282 |
| PCP | 34770 | 34842 | 35413 | 28960 | 35753 | 33437 | 14050 | 27805 | 38396 | 16510 |
| THC | 35966 | 36591 | 36809 | 29924 | 37452 | 34817 | 30446 | 36456 | 40326 | 32159 |
| XTC | 28212 | 16204 | 28446 | 27219 | 20748 | 22127 | 18062 | 28133 | 38420 | 21103 |
| MATRIX | 8442 | 8272 | 8667 | 6641 | 8647 | 8133 | 9829 | 9697 | 9689 | 9915 |

| | \multicolumn{10}{c}{520 Corrected Data [($520_{sample}/520_{Matrix}$)]} | | | | | | | | | |
|---|---|---|---|---|---|---|---|---|---|---|
| | 917 | 920 | 926 | 936 | 937 | 990 | PLUS 50 | MINUS 50 | NEG | CUTOFF |
| AMP | 2.082 | 1.642 | 1.799 | 4.822 | 1.911 | 2.133 | 1.930 | 3.636 | 4.531 | 2.254 |
| COC | 4.506 | 4.499 | 4.455 | 4.613 | 4.395 | 4.452 | 3.029 | 3.757 | 4.314 | 3.296 |
| MET | 1.796 | 1.862 | 1.868 | 5.114 | 1.881 | 1.800 | 2.120 | 3.821 | 5.578 | 2.489 |
| MOR | 4.316 | 4.396 | 4.321 | 4.602 | 4.359 | 4.281 | 1.788 | 2.959 | 4.222 | 2.046 |
| PCP | 4.119 | 4.212 | 4.086 | 4.361 | 4.135 | 4.111 | 1.429 | 2.867 | 3.963 | 1.665 |
| THC | 4.260 | 4.423 | 4.247 | 4.506 | 4.331 | 4.281 | 3.098 | 3.760 | 4.162 | 3.243 |
| XTC | 3.342 | 1.959 | 3.282 | 4.099 | 2.399 | 2.721 | 1.838 | 2.901 | 3.965 | 2.128 |

| | \multicolumn{10}{c}{Interpretation of Results} | | | | | | | | | |
|---|---|---|---|---|---|---|---|---|---|---|
| | 917 | 920 | 926 | 936 | 937 | 990 | PLUS 50 | MINUS 50 | NEG | CUTOFF |
| AMP | POS | POS | POS | — | POS | POS | POS | — | — | — |
| COC | — | — | — | — | — | — | POS | — | — | — |
| MET | POS | POS | POS | — | POS | POS | POS | — | — | — |
| MOR | — | — | — | — | — | — | POS | — | — | — |
| PCP | — | — | — | — | — | — | POS | — | — | — |
| THC | — | — | — | — | — | — | POS | — | — | — |
| XTC | — | POS | — | — | — | — | POS | — | — | — |

Correlation of Results by GC/MS

Sample 917—Homogeneous Assay Positive (POS) for Amphetamine (AMP), Methamphetamine (MET).

GC/MS results—Amphetamine (AMP) 57 ng/mL, Methamphetamine (MET) 600 ng/mL.

Sample 920—Homogeneous Assay Positive (POS) for Amphetamine (AMP), Methamphetamine (MET), 3,4-methylenedioxy-N-methylamphetamine (XTC).

GC/MS results—Amphetamine (AMP) 336 ng/mL, Methamphetamine (MET) 4435 ng/mL.

Homogeneous Assay POS for 3,4-methylenedioxy-N-methylamphetamine (XTC) is due to cross-reactivity of that antibody with Methamphetamine (MET) at high concentrations.

Sample 926—Homogeneous Assay Positive (POS) for Amphetamine (AMP), Methamphetamine (MET).

GC/MS results—Amphetamine (AMP) 110 ng/mL, Methamphetamine (MET) 449 ng/mL.

Sample 936—Homogeneous Assay Negative (−) for all drugs tested.

Sample 937—Homogeneous Assay Positive (POS) for Amphetamine (AMP), Methamphetamine (MET).

GC/MS results—Amphetamine (AMP) 77 ng/mL, Methamphetamine (MET) 2127 ng/mL.

Sample 990—Homogeneous Assay Positive (POS) for Amphetamine (AMP), Methamphetamine (MET).

GC/MS results—Amphetamine (AMP) 58 ng/mL, 993 ng/mL.

PLUS 50—Controls containing 150% cutoff concentrations tested positive by homogeneous assay for all drugs as expected.

MINUS 50—Controls containing 50% cutoff concentrations tested negative by homogeneous assay for all drugs as expected.

NEG—Negative calibrator tested negative by homogeneous assay for all drugs as expected.

CUTOFF—Cutoff calibrator was used to determine cutoff level for determining positive and negative test results.

Discussion of Results

In this example the corrected data correctly identified the presence of Amphetamine (AMP) and Methamphetamine (MET) at concentrations above 50 ng/mL when compared to GC/MS quantitation. For sample 936, the raw data indicated that Cocaine (COC) and Tetrahydrocannabinol (THC) were positive relative to the cutoff calibrator. The corrected data indicates that this sample was negative for Cocaine (COC) and Tetrahydrocannabinol (THC).

Figure 5:
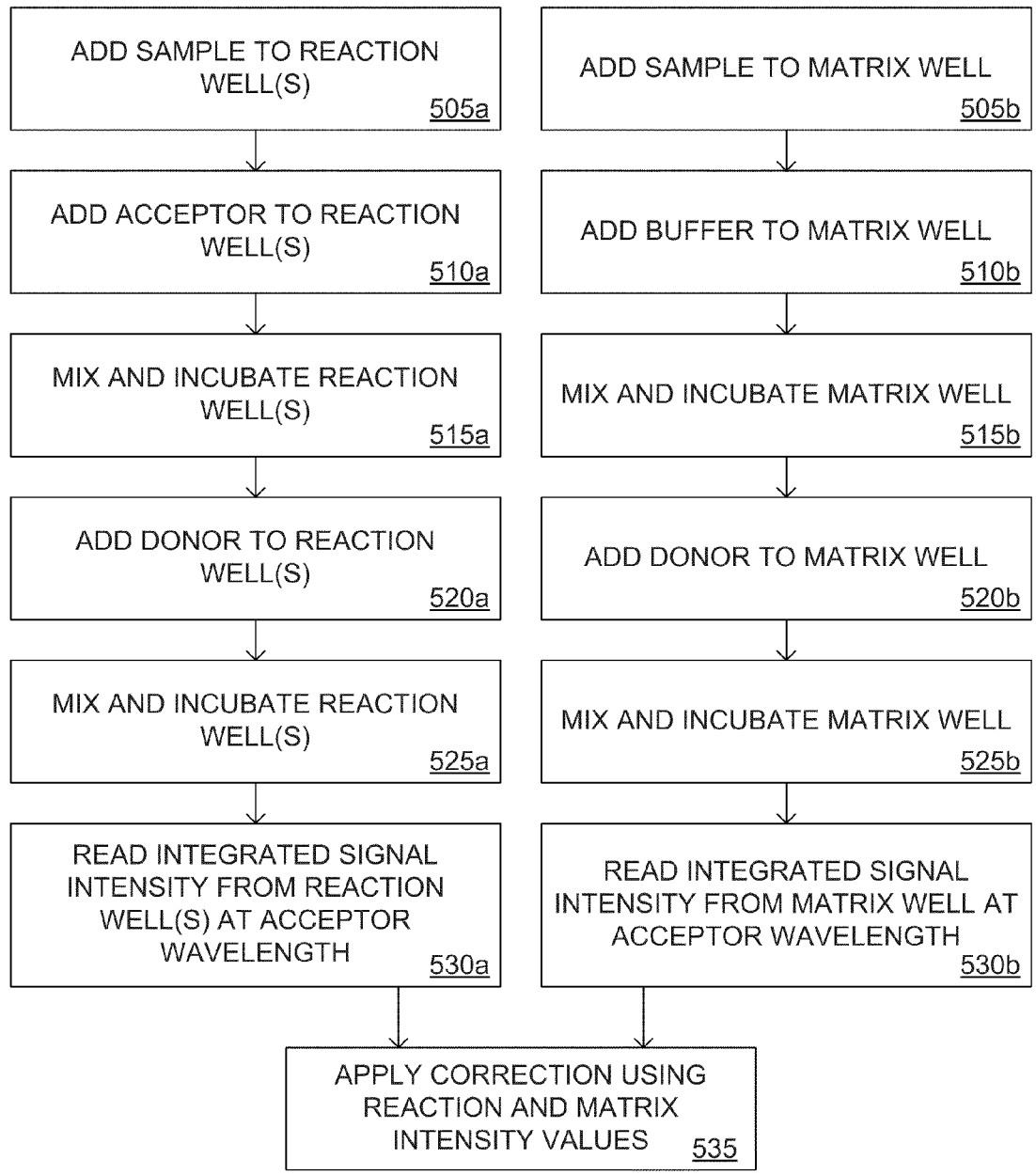
FIG. 5 shows a flow diagram for a multi-volume homogeneous assay in accordance with an embodiment of the present invention.

FIG. 5 shows a flow diagram 500 for an embodiment of a corrected homogeneous assay using at least two wells and a single wavelength for characterization. The assay uses one matrix well and may use one or more reaction wells. Although the examples provided above referred specifically to wells in a microtiter plate, a "well" in the general sense refers to a discrete volume of liquid.

At steps 505a and 505b, a sample is added to the respective reaction and matrix wells. The sample is a biological fluid (e.g., oral fluid) for which the presence of a specific analyte is to be determined.

At step 510a an acceptor reagent including an analyte-specific antibody-luminophore is added to the reaction well. The luminophore may be an organic dye (e.g., fluorescein). At optional step 510b a buffer may be added to the matrix well in an amount similar to the amount of acceptor reagent added to the reaction well in step 510a.

At steps 515a and 515b the respective reaction and matrix wells may be mixed and incubated. Incubation typically involves time-at-temperature, and mixing may be assisted by gentle shaking. When the reaction and matrix wells reside on a single microtiter plate, steps 515a and 515b will typically be identical; however, since the reaction well involves a binding reaction with the acceptor reagent that is not present in the matrix well, the degree of mixing (if used) and the time-at-temperature may not necessarily be identical.

At steps 520a and 520b a donor reagent is added to the respective reaction and matrix wells. The donor reagent includes at least one competitor conjugate donor. The competitor conjugate donor may include a lanthanide dye.

At steps 525a and 525b the respective reaction and matrix wells may be mixed and incubated. Incubation typically involves time-at-temperature, and mixing may be assisted by gentle shaking. When the reaction and matrix wells reside on a single microtiter plate, steps 515a and 515b will typically be identical; however, since the reaction well involves a competitive binding reaction between the acceptor reagent, and the sample and donor reagent that is not present in the matrix well, the degree of mixing (if used) and the time-at-temperature may not necessarily be identical.

Figure 3:
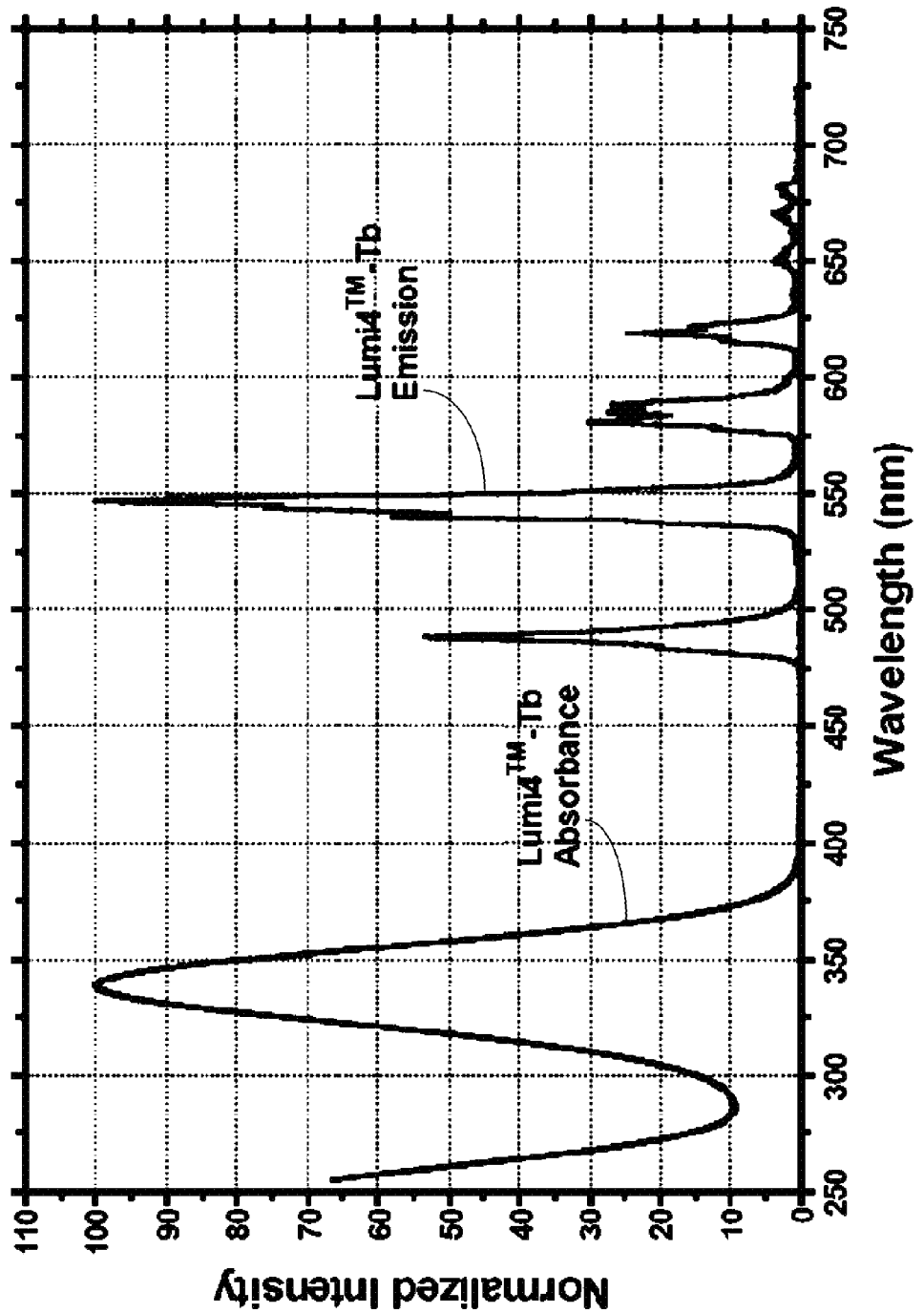
FIG. 3 shows the absorption and emission spectra for LUMI4-TB.
Figure 4A:
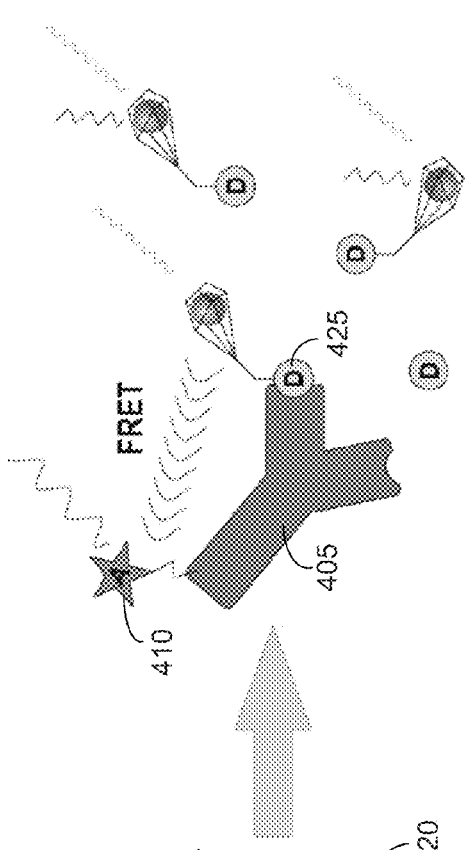
FIG. 4A shows a schematic representation of a system with an antibody-luminophore and competitor conjugate donor in the presence of a relatively low concentration of analyte.
Figure 4B:
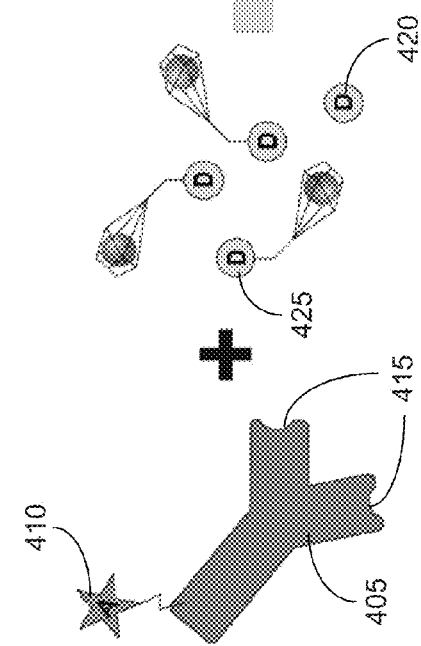
FIG. 4B shows a schematic of the luminescent behavior of the system shown in FIG. 4A.
Figure 4C:
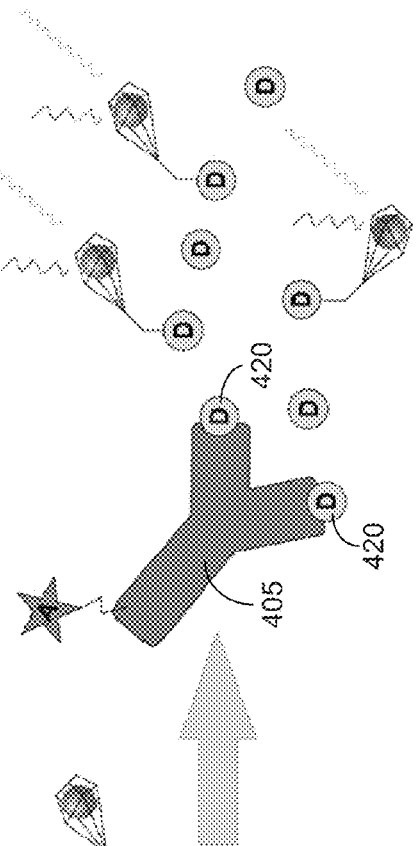
FIG. 4C shows a schematic representation of a system with an antibody-luminophore and competitor conjugate donor in the presence of a relatively high concentration of analyte.
Figure 4D:
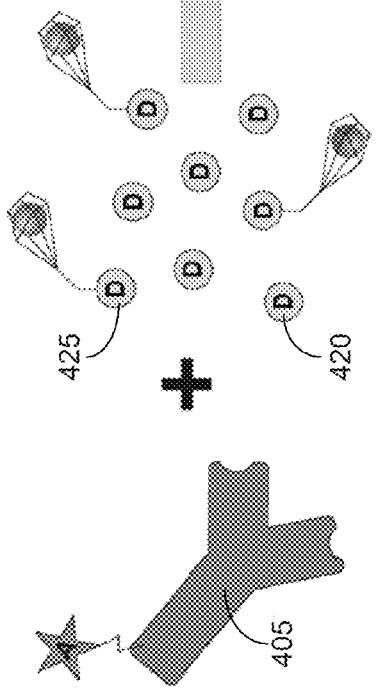
FIG. 4D shows a schematic of the luminescent behavior of the system shown in FIG. 4C.

At steps 530a and 530b the respective signal intensity of the reaction well and matrix well are measured at a characteristic wavelength associated with the acceptor reagent luminophore. As can be seen from the above examples and Prior Art FIG. 3, the emission of the donor luminophore (e.g., LUMI4-TB) at the acceptor wavelength (e.g., 520 nm) may be more than an order of magnitude lower than the emission at a peak wavelength associated with the donor luminophore (e.g., ~550 nm for LUMI4-TB).

At step 535 a correction is applied to the intensity measurement obtained from the reaction well using the intensity measurement obtained from the matrix well. For example, the reaction well intensity value may be divided by the matrix well intensity value to produce the corrected value.

Figure 6:
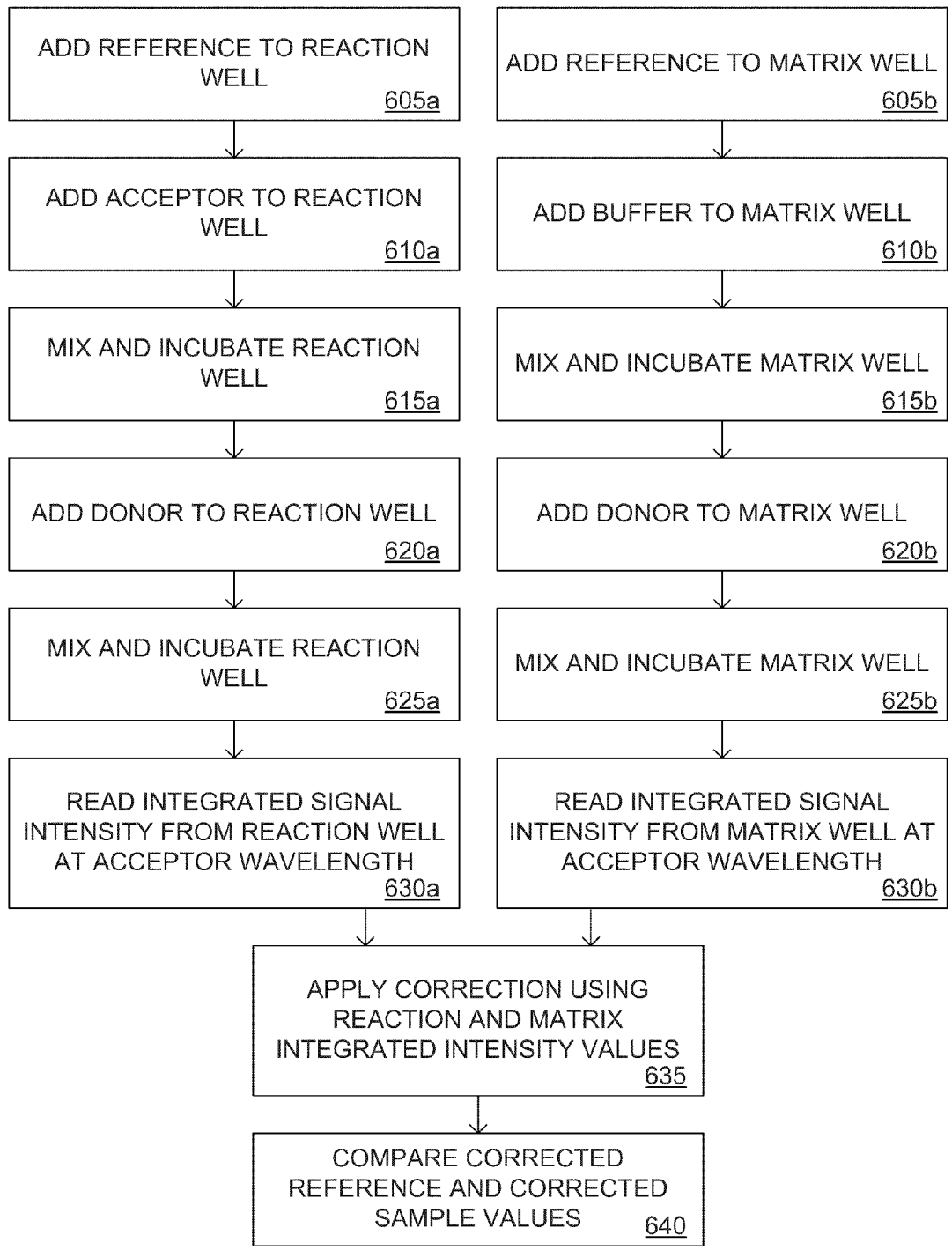
FIG. 6 shows a flow diagram for a multi-volume homogeneous assay incorporating a reference in accordance with an embodiment of the present invention.

FIG. 6 shows a flow diagram 600 for an embodiment of a corrected homogeneous test assay that utilizes the corrected value obtained from the homogeneous assay shown in FIG. 5. The corrected homogeneous test assay includes a series of steps similar to the steps shown in FIG. 5, except that the sample, which is typically of an unknown composition, is replaced by a reference with a known composition (e.g., predetermined analyte content).

At steps 605a and 605b, a reference is added to the respective reaction and matrix wells. At step 610a an acceptor reagent including an analyte-specific antibody-luminophore is added to the reaction well. The luminophore may be an organic dye (e.g., fluorescein). At optional step 610b a buffer may be added to the matrix well in an amount similar to the amount of acceptor reagent added to the reaction well in step 610a.

At steps 615a and 615b the respective reaction and matrix wells may be mixed and incubated. Incubation typically involves time-at-temperature, and mixing may be assisted by gentle shaking. When the reaction and matrix wells reside on a single microtiter plate, steps 615a and 615b will typically be identical; however, since the reaction well involves a binding reaction with the acceptor reagent that is not present in the matrix well, the degree of mixing (if used) and the time-at-temperature may not necessarily be identical.

At steps 620a and 620b a donor reagent is added to the respective reaction and matrix wells. The donor reagent includes at least one competitor conjugate donor. The competitor conjugate donor may include a lanthanide dye.

At steps 625a and 625b the respective reaction and matrix wells may be mixed and incubated. Incubation typically involves time-at-temperature, and mixing may be assisted by gentle shaking. When the reaction and matrix wells reside on a single microtiter plate, steps 615a and 615b will typically be identical; however, since the reaction well involves a competitive binding reaction between the acceptor reagent, and the sample and donor reagent that is not present in the matrix well, the degree of mixing (if used) and the time-at-temperature may not necessarily be identical.

At steps 630a and 630b the respective signal intensity of the reaction well and matrix well are measured at a characteristic wavelength associated with the acceptor reagent luminophore. As can be seen from the above examples and Prior Art FIG. 3, the emission of the donor luminophore (e.g., LUMI4-TB) at the acceptor wavelength (e.g., 520 nm) may be more than an order of magnitude lower than the emission at a peak wavelength associated with the donor luminophore (e.g., ~550 nm for LUMI4-TB).

At step 635 a correction is applied to the intensity measurement obtained from the reaction well using the intensity measurement obtained from the matrix well. For example, the reaction well intensity value may be divided by the matrix well intensity value to produce the corrected value. At step 640 the corrected reference value obtained in step 635 is compared to the corrected sample value obtained in step 535 of FIG. 5.

While the invention has been described in detail with reference to preferred embodiments thereof, it will be apparent to one skilled in the art that various changes can be made, and equivalents employed, without departing from the scope of the invention.

What is claimed:

1. A method for performing a homogeneous biological assay comprising:
   preparing at least one reaction volume and a matrix volume wherein said reaction volume and said matrix volume each comprise a biological fluid;
   adding an acceptor reagent to said reaction volume;
   adding a lanthanide donor reagent to said reaction volume;
   adding a lanthanide donor reagent to said matrix volume;
   applying an optical excitation to said reaction volume;
   obtaining a first integrated intensity value for the luminescent intensity of said reaction volume at a single characteristic emission wavelength of said acceptor reagent;
   applying an optical excitation to said matrix volume;
   obtaining a second integrated intensity value for the luminescent intensity of said matrix volume at said single characteristic emission wavelength of said acceptor reagent, wherein said luminescent intensity of said matrix volume comprises luminescent emission from said lanthanide donor reagent at said single characteristic emission wavelength of said acceptor reagent; and
   correcting said first integrated intensity value by applying a mathematical expression to said first integrated intensity wherein said mathematical expression comprises said second integrated intensity value.

2. The method of claim 1 wherein said biological fluid is an oral fluid.

3. The method of claim 1 wherein said acceptor reagent comprises a fluorescent dye.

4. The method of claim 3 wherein said acceptor reagent comprises fluorescein.

5. The method of claim 1 wherein said mathematical expression comprises dividing said first integrated intensity value by said second integrated intensity value.

6. The method of claim 1 wherein said donor reagent comprises a terbium complex.

7. The method of claim 1 further comprising mixing said reaction volume.

8. The method of claim 1 further comprising incubating said reaction volume.

9. The method of claim 1 further comprising mixing said matrix volume.

10. The method of claim 1 further comprising incubating said matrix volume.

11. The method of claim 1 further comprising adding a buffer to said matrix volume.

12. The method of claim 1 wherein the emissive intensity of said donor reagent at said single characteristic emission wavelength of said acceptor reagent is less than one tenth the emissive intensity at a emissive peak of said donor reagent.

13. The method of claim 12 wherein the emissive intensity of said donor reagent at said single characteristic emission wavelength of said acceptor reagent is less than one fiftieth the emissive intensity at a characteristic emissive peak of said donor reagent.

14. The method of claim 1 further comprising:
   preparing at least one reference reaction volume and a reference matrix volume wherein said reference reaction volume and said reference matrix volume each comprise a known quantity of an analyte;
   adding an acceptor reagent to said reference reaction volume;
   adding a donor reagent to said reference reaction volume;
   adding a donor reagent to said reference matrix volume;
   applying an optical excitation to said reference reaction volume;
   obtaining a third integrated intensity value for the luminescent intensity of said reference reaction volume at said single characteristic emission wavelength of said acceptor reagent;
   applying an optical excitation to said reference matrix volume;
   obtaining a fourth integrated intensity value for the luminescent intensity of said reference matrix volume at said single characteristic emission wavelength of said acceptor reagent;
   applying a correction to said third integrated intensity value based upon said fourth integrated intensity value to obtain a corrected reference reaction integrated intensity value; and
   comparing said corrected reaction integrated intensity value to said corrected reference reaction integrated intensity value.

15. The method of claim 14 wherein said biological fluid is an oral fluid.

16. The method of claim 14 wherein said acceptor reagent comprises a fluorescent dye.

17. The method of claim 14 wherein said mathematical expression comprises dividing said first integrated intensity value by said second integrated intensity value.

18. The method of claim 14 wherein said donor reagent comprises a terbium complex.

19. The method of claim 14 wherein the emissive intensity of said donor reagent at said single characteristic emission wavelength of said acceptor reagent is less than one tenth the emissive intensity at a characteristic emissive peak of said donor reagent.

20. The method of claim 14 wherein the emissive intensity of said donor reagent at said single characteristic emission wavelength of said acceptor reagent is less than one fiftieth the emissive intensity at a characteristic emissive peak of said donor reagent.

* * * * *